(12) United States Patent
Jensen et al.

(10) Patent No.: US 9,108,006 B2
(45) Date of Patent: Aug. 18, 2015

(54) MEDICAL DEVICE WITH VALUE SENSOR

(75) Inventors: Peter Lundholm Jensen, Copenhagen (DK); Kristian Glejbøl, Glostrup (DK); Lars Peter Klitmose, Gentofte (DK); Salim Bouaidat, Copenhagen (DK)

(73) Assignee: Novo Nordisk A/S, Bagsvaerd (DK)

(*) Notice: Subject to any disclaimer, the term of this patent is extended or adjusted under 35 U.S.C. 154(b) by 1280 days.

(21) Appl. No.: 12/673,530

(22) PCT Filed: Aug. 18, 2008

(86) PCT No.: PCT/EP2008/060813
§ 371 (c)(1),
(2), (4) Date: Jul. 13, 2011

(87) PCT Pub. No.: WO2009/024562
PCT Pub. Date: Feb. 26, 2009

(65) Prior Publication Data
US 2011/0264033 A1      Oct. 27, 2011

Related U.S. Application Data (60) Provisional application No. 60/956,951, filed on Aug. 21, 2007.

(30) Foreign Application Priority Data

Aug. 17, 2007  (EP) ................................. 07114527

(51) Int. Cl.
*A61M 5/31*       (2006.01)
*A61M 5/48*       (2006.01)
(Continued)

(52) U.S. Cl.
CPC ............. *A61M 5/486* (2013.01); *A61M 5/1452* (2013.01); *A61M 5/16854* (2013.01);
(Continued)

(58) Field of Classification Search
CPC ......... A61M 5/24; A61M 5/28; A61M 5/486; A61M 5/365; A61M 5/16854; A61M 5/1452; A61M 2005/16863; A61M 2205/15; A61M 2205/332; A61M 2205/35; A61M 2205/3569; A61M 2205/3592; A61M 2205/6054; A61M 2205/8243
USPC ......... 604/65–67, 86, 88, 131, 181, 185–187, 604/189, 200–206
See application file for complete search history.

(56) References Cited

U.S. PATENT DOCUMENTS

| | | |
|---|---|---|
| 3,944,843 A | 3/1976 | Vaz Martins |
| 4,515,584 A | 5/1985 | Abe et al. |

(Continued)

FOREIGN PATENT DOCUMENTS

| | | |
|---|---|---|
| CA | 2359375 | 7/2000 |
| DE | 3236374 | 4/1984 |

(Continued)

OTHER PUBLICATIONS

Beckmann, Sensors, Memory, Circuits, Polyapply Newsletter, vol. 1(3) (2006).

(Continued)

*Primary Examiner* — Matthew F Desanto
(74) *Attorney, Agent, or Firm* — Wesley Nicolas (57) ABSTRACT

A RFID comprising a value sensor such as a pressure sensor is integrated with a liquid drug container to enable wireless pressure or other drug relevant parameter value monitoring and code-matching of drug container to a medical delivery device.

16 Claims, 5 Drawing Sheets

(51) Int. Cl.
*A61M 5/145* (2006.01)
*A61M 5/168* (2006.01)
*G06F 19/00* (2011.01)
*A61M 5/24* (2006.01)
*A61M 5/36* (2006.01)

(52) U.S. Cl.
CPC .............. *G06F 19/3468* (2013.01); *A61M 5/24* (2013.01); *A61M 5/365* (2013.01); *A61M 2005/16863* (2013.01); *A61M 2005/3125* (2013.01); *A61M 2205/15* (2013.01); *A61M 2205/332* (2013.01); *A61M 2205/3324* (2013.01); *A61M 2205/3331* (2013.01); *A61M 2205/3368* (2013.01); *A61M 2205/35* (2013.01); *A61M 2205/3569* (2013.01); *A61M 2205/3592* (2013.01); *A61M 2205/6054* (2013.01); *A61M 2205/8243* (2013.01)

(56) References Cited

U.S. PATENT DOCUMENTS

| | | |
|---|---|---|
| 4,634,431 A | 1/1987 | Whitney et al. |
| 4,812,724 A | 3/1989 | Langer et al. |
| 4,838,860 A | 6/1989 | Groshong et al. |
| 4,871,351 A | 10/1989 | Feingold |
| 4,898,578 A | 2/1990 | Rubalcaba |
| 4,950,246 A | 8/1990 | Muller |
| 5,135,485 A | 8/1992 | Cohen et al. |
| 5,163,904 A | 11/1992 | Lampropoulos et al. |
| 5,221,268 A | 6/1993 | Barton et al. |
| 5,320,609 A | 6/1994 | Haber et al. |
| 5,536,249 A | 7/1996 | Castellano et al. |
| 5,593,390 A | 1/1997 | Castellano et al. |
| 5,628,309 A | 5/1997 | Brown |
| 5,662,612 A | 9/1997 | Niehoff |
| 5,681,285 A | 10/1997 | Ford et al. |
| 5,720,733 A | 2/1998 | Brown |
| 5,728,074 A | 3/1998 | Castellano et al. |
| 5,741,211 A | 4/1998 | Renirie et al. |
| 5,820,602 A | 10/1998 | Kovelman et al. |
| 5,879,360 A | 3/1999 | Crankshaw |
| 5,879,630 A | 3/1999 | Lescouzeres et al. |
| 5,928,201 A | 7/1999 | Poulsen et al. |
| 5,933,671 A | 8/1999 | Stephany et al. |
| 5,971,963 A | 10/1999 | Choi |
| 5,989,221 A | 11/1999 | Hjertman |
| 5,998,989 A | 12/1999 | Lohberg |
| 6,019,745 A | 2/2000 | Gray |
| 6,110,148 A | 8/2000 | Brown et al. |
| 6,161,364 A | 12/2000 | Kolberg |
| 6,268,722 B1 | 7/2001 | Kogure et al. |
| 6,340,357 B1 | 1/2002 | Poulsen et al. |
| 6,391,005 B1 | 5/2002 | Lum et al. |
| 6,547,755 B1 | 4/2003 | Lippe et al. |
| 6,558,358 B2 * | 5/2003 | Rosoff et al. ............... 604/200 |
| 6,585,698 B1 | 7/2003 | Packman et al. |
| 6,673,033 B1 | 1/2004 | Sciulli et al. |
| 7,080,936 B1 | 7/2006 | Simpson |
| 7,195,609 B2 | 3/2007 | Huegli |
| 8,409,142 B2 * | 4/2013 | Causey et al. ............... 604/151 |
| 2002/0002326 A1 | 1/2002 | Causey, III et al. |
| 2002/0020654 A1 | 2/2002 | Eilersen |
| 2003/0009133 A1 | 1/2003 | Ramey |
| 2003/0073954 A1 | 4/2003 | Moberg et al. |
| 2003/0114800 A1 | 6/2003 | Veasey et al. |
| 2003/0216663 A1 | 11/2003 | Jersey-Willuhn et al. |
| 2003/0233075 A1 | 12/2003 | Huegli |
| 2004/0010204 A1 | 1/2004 | Weber et al. |
| 2004/0024361 A1 | 2/2004 | Fago et al. |
| 2004/0051368 A1 | 3/2004 | Caputo et al. |
| 2004/0158304 A1 | 8/2004 | Cory et al. |
| 2004/0171983 A1 | 9/2004 | Sparks et al. |
| 2004/0207385 A1 | 10/2004 | Gafner et al. |
| 2004/0230157 A1 | 11/2004 | Perry et al. |
| 2004/0267207 A1 | 12/2004 | Veasey et al. |
| 2008/0306443 A1 * | 12/2008 | Neer et al. ............... 604/121 |

FOREIGN PATENT DOCUMENTS

| | | |
|---|---|---|
| DE | 3923079 | 1/1991 |
| DE | 19503230 | 8/1996 |
| DE | 10201875 | 5/2003 |
| DE | 102004046003 | 3/2006 |
| DK | 200100240 | 2/2001 |
| DK | 2005/00116 | 6/2005 |
| EP | 017318 | 10/1980 |
| EP | 338806 | 10/1989 |
| EP | 387854 | 9/1990 |
| EP | 422482 | 4/1991 |
| EP | 454331 | 10/1991 |
| EP | 615762 | 9/1994 |
| EP | 1074273 | 2/2001 |
| EP | 1095668 | 5/2001 |
| EP | 1557163 | 7/2005 |
| EP | 1557189 | 7/2005 |
| EP | 1723977 | 11/2006 |
| EP | 1728529 | 12/2006 |
| EP | 1782853 | 5/2007 |
| EP | 2000161 | 12/2008 |
| FR | 2622457 | 5/1989 |
| FR | 2740345 | 4/1997 |
| GB | 2153445 | 8/1985 |
| GB | 2229497 | 9/1990 |
| GB | 2309644 | 8/1997 |
| IN | 165367 | 3/1986 |
| JP | 56-163486 | 12/1981 |
| JP | 01-100495 | 4/1989 |
| JP | 02-126184 | 5/1990 |
| JP | 02-182267 | 7/1990 |
| JP | 7-502678 | 3/1995 |
| JP | 09166474 | 6/1997 |
| JP | 3017167 | 11/1999 |
| JP | 2006250582 | 9/2006 |
| WO | WO 85/02256 | 5/1985 |
| WO | WO90/09202 | 8/1990 |
| WO | WO93/01573 | 1/1993 |
| WO | WO95/24233 | 9/1995 |
| WO | WO97/30742 | 8/1997 |
| WO | WO 99/07425 | 2/1999 |
| WO | WO99/15214 | 4/1999 |
| WO | WO99/65548 | 12/1999 |
| WO | WO0037129 | 6/2000 |
| WO | WO01/26710 | 4/2001 |
| WO | WO02/05876 | 1/2002 |
| WO | WO0224257 | 3/2002 |
| WO | WO02/053214 | 7/2002 |
| WO | WO02/064196 | 8/2002 |
| WO | WO02092153 | 11/2002 |
| WO | WO03/057283 | 7/2003 |
| WO | WO03/063680 | 8/2003 |
| WO | WO97/33638 | 9/2003 |
| WO | WO03/099357 | 12/2003 |
| WO | WO2004/028598 | 4/2004 |
| WO | WO2004/080306 | 9/2004 |
| WO | WO2004/084795 | 10/2004 |
| WO | WO2004/095379 | 11/2004 |
| WO | WO2005/089835 | 9/2005 |
| WO | WO2006/039930 | 4/2006 |
| WO | WO2006/045425 | 5/2006 |
| WO | WO2006/045525 | 5/2006 |
| WO | WO2006/045529 | 5/2006 |
| WO | WO2006/069454 | 7/2006 |
| WO | WO2006/076921 | 7/2006 |
| WO | WO2006/116997 | 11/2006 |
| WO | WO2006/128794 | 12/2006 |
| WO | WO2007/030957 | 3/2007 |
| WO | WO2007/041843 | 4/2007 |
| WO | WO2007/107558 | 9/2007 |
| WO | WO2007/107561 | 9/2007 |
| WO | WO2007/134954 | 11/2007 |
| WO | WO2008/037801 | 4/2008 |
| WO | WO2008057223 | 5/2008 |

(56) References Cited

FOREIGN PATENT DOCUMENTS

OTHER PUBLICATIONS

Trankler, Hans-Rolf, R. Oldenbourg, Verlag, Munchen, Wien (Explained in the Opposition in Related European Patent Application EP 07711784 5 of Sep. 19, 2008).
English Abstract of DE10201875.
English Abstract of DE102004046003.
English Abstract of DE19503230.
English Abstract of DE3923079.
English Abstract of DE3236374.
English Abstract of EP387854.
English Abstract of EP422482.
English Abstract of FR2622457.
English Abstract of FR2740345.
English Abstract of IN165367.
Machine Translation of JP09166474.
English Abstract of JP2006250582.
English Abstract of JP02-126184.
English Abstract of JP56-163486.
Englisii Abstract of JP3017167.
English Abstract of JP01-100495.
English Abstract of JP02-182267.
Common Insulin Injection Challenges: http://www.bd.com/us/diabetes/page.aspx?cat=7001&id=7265.
Gnanalingham, M.G. et al., Accuracy and Reproducibility of Low Dose Insulin Administration Using Pen-Injectors and Syringes, Downloaded from adc.bmj.com on January 9, 2008.
Annersten, M. et al., Insulin Pens Dribble From the Tip of the Needle After Injection, Practical Diabetes Int., vol. 17(4), pp. 109-111 (2000).
Office Action in U.S. Appl. No. 09/137,014, filed Aug. 20, 1998; Inventors: Jensen et al., of Jul. 9, 1999.
Office Action in U.S. Appl. No. 09/137,014, filed Aug. 20, 1998; Inventors: Jensen et al., of Feb. 18, 2000.
Office Action in U.S. Appl. No. 10/076,025, filed Feb. 13, 2002; Inventors: Larsen et al., of Nov. 28, 2003.
Office Action in U.S. Appl. No. 10/076,025, filed Feb. 13, 2002; Inventors: Larsen et al., of Nov. 15, 2004.
Office Action in U.S. Appl. No. 12/293,247, filed Sep. 16, 2008; Inventor: Andre Larsen, of Nov. 25, 2009.
Final Action in U.S. Appl. No. 12/293,247, filed Sep. 16, 2008; Inventor: Andre Larsen, of Jun. 7, 2010.
Opposition in Related European Patent Application EP 02711784.5 of Sep. 19, 2008.
Search Report Issued in Connection With European Appln No. 06005602.5, Mailed Oct. 16, 2006.
Search Report Issued in Connection With PCT Appln. No. PCT/EP2007/052630, Mailed Nov. 12, 2007.

* cited by examiner

MEDICAL DEVICE WITH VALUE SENSOR

CROSS-REFERENCE TO RELATED APPLICATIONS

This application is a 35 U.S.C. §371 national stage application of International Patent Application PCT/EP2008/060813 (published as WO 2009/024562), filed AUG. 18, 2008, which claimed priority of European Patent Application 07114527.0, filed AUG. 17, 2007; this application further claims priority under 35 U.S.C. §119 of U.S. Provisional Application 60/956,951, filed Aug. 21, 2007.

TECHNICAL FIELD

The present invention relates to a medical delivery device for cooperating with a liquid drug container, the medical delivery device or the container having a sensor system integrated and being able to communicate information about a measured physical or chemical parameter value relevant to the drug or drug dispensing from the integrated sensor system to a control circuit of the medical delivery device.

BACKGROUND OF THE INVENTION

A medical drug delivery device such as for instance an insulin injection device or an insulin pump for substantially continuous delivery of insulin, or any other medical liquid drug delivery device need a high security level to ensure that the correct dose size or volume flow of liquid drug is delivered to the user, and that there is at all delivered drug to the user. A potential error in a liquid drug delivery device is an occlusion anywhere in the outlet path from the drug container to the delivery point such as the tissue or a vein of a user. For instance an injection needle mounted in fluid connection to a drug cartridge through a penetrable septum can be occluded, or a butterfly needle luer lock connected to a liquid drug container can be occluded. Another problem is the occurrence of a leak in the drug container itself or along the fluid drug delivery line. A security system is therefore needed to sense if an occlusion or a leak occurs in the medical drug delivery device so the appropriate action can be taken, such as change of needle and recalculation of an appropriate dose. U.S. Pat. No. 7,195,609 addresses the problem of detecting an occlusion or a leak by incorporating a sensor in the movable piston of a product container and connecting the sensor via wires for monitoring the pressure in the drug container. However U.S. Pat. No. 7,195,609 poses the problem of connecting the sensor via wires which are complicated and expensive to manufacture and mount and poses a security problem as the wires can be broken or the electrical connections can be poor or corrode.

The amount of drug delivered is important, but further the correct type of drug is crucial and poses a security issue in medical drug delivery devices. This problem is discussed in WO 9965548, which discloses a way to share information on syringe configuration between syringes and injector systems.

Thus, there is a need for a simple and cost effective system to ensure correct dose size, reliability of dose delivery and correct type of drug delivered from a medical liquid drug delivery.

SUMMARY OF THE INVENTION

It is an object of the present invention to provide a safe, simple and low cost system for monitoring the delivery of a fluid drug from a medical drug delivery device.

It is a further object of the present invention to provide a safe, simple and low cost system for identifying the type of drug contained in a liquid drug container and further information and communicate the information to the medical drug delivery device.

It is yet a further object of the present invention to provide the possibility for monitoring physical and chemical values related to the contained drug and communicate this information to the medical drug delivery device in a safe, simple and low cost way.

In accordance with a first aspect, the invention relates to a medical delivery device for delivering a fluid drug from a container, the medical delivery device comprising control circuitry and a sensor system adapted to measure at least one physical or chemical parameter value related with fluid delivery and/or the fluid drug, said sensor system being adapted to transfer said at least one measured parameter value to the control circuitry, wherein a) the sensor system comprises an electrically operable transponder device to emit data including the at least one measured parameter value in response to activation by a suitable field, and wherein b) the control circuitry comprises activation means operable to emit the field suitable to cause the electrically operable transponder device to emit the at least one measured parameter value, and receiving means for receiving the. data thus emitted.

In one form, the medical delivery device comprises an actuator for transferring the fluid drug through an outlet wherein the above mentioned sensor system is coupled to or comprised within said actuator. In other embodiments, the sensor system is comprised within or coupled to the medicament container. The actuator may take the form of a plunger rod for pressing forward a plunger of a medicament cartridge. In such systems, the sensor system may comprise a sensor adapted to measure a force, or and on/off switch for detecting whether plunger rod/plunger contact is obtained or maintained. Additionally, or as an alternative, the sensor system may be adapted to monitor one or more of the parameter values relating to temperature, electrical resistance, electrical conductivity, capacitance, pH, optical translucency and dissolved oxygen.

In one embodiment, the medical delivery device comprises a first housing part being coupled or being coupleable to the drug container, where the first housing part further includes an actuator mechanism for transferring fluid drug from the container through an outlet, and wherein the control circuitry is contained in a second housing part of the medical delivery device, the second housing part being releasably attachable to the first housing part. In one embodiment, such system may include a pre-filled injection device, i.e. a disposable device where the medicament container is non-exchangeable or non-fillable, the injection device being accommodated in the first housing part to cooperate with an auxilliary device being accommodated in the second housing part where the injection device and the auxilliary device constitutes a medical delivery device according to the appended claims when they are mutually coupled/attached. In such device, the auxilliary device may be adapted to be used with a series of pre-filled injection devices, one after another. The electric circuitry included in the first housing may be reduced to a minimum, e.g. only holding the sensor system, but the medical delivery device may provide additional electronic functionality when the injection device it is coupled to the auxilliary device holding additional circuitry including the above mentioned control circuitry. In this way, the auxilliary device may employ more extensive and thus expensive components which provides for additional processing as well as user communication features, which may only be economically viable in durable devices.

In further embodiments, the medical delivery device includes a single hand-held housing which includes the drug container or which is coupleable to the drug container, the single hand-held housing further holding an actuator mechanism for transferring fluid drug from the container through an outlet and further holding the control circuitry. Still, in such an embodiment, the sensor system provides a more flexible way of monitoring different conditions during use of the device, in particular when monitored components are situated remote from a central electronic circuitry or when monitored components do not allow easy connection by conventional wiring.

In a second aspect of the invention, the invention relates to a medicament container adapted to contain a fluid drug and adapted to cooperate with a medical delivery device for delivering medicament from the container, the medicament container having a sensor system adapted to measure at least one physical or chemical parameter value related with the container and/or the fluid contained therein, wherein the sensor system comprises an electrically operable transponder device to emit the at least one measured parameter value in response to activation by a suitable field applied by an external means.

In some embodiments, the medicament container is a cartridge closed in one end by a piercable septum and closed in the other end by a plunger slideably arranged with respect to the cartridge wall.

In other embodiments, the medicament container forms a flexible reservoir having at least one wall portion made from a flexible material or having all wall sections made of a flexible material.

Embodiments providing cartridges or flexible reservoirs may include the sensor system to be attached to the container, it may be comprised within the drug container or it may form an integral part of the container, such as part of the walls forming the compartment, or part of a piercable septum for connection to a needle etc.

The medicament container according to the second aspect, may comprise a pressure or force sensor, whereby the pressure in the fluid drug or the force acting on the drug via an actuator of the cooperating medical delivery device can be monitored.

Other physical or chemical parameter values may be monitored by the sensor system. For example, the sensor system may be adapted to monitor one or more of the parameter values selected from the group consisting of temperature, electrical resistance, electrical conductivity, capacitance, optical translucency, pH and dissolved oxygen.

Further, the sensor unit may be adapted to store a code related to the drug. The code can contain information about type of drug, production date and time, or any other relevant information; also the code can be a safety code which ensures safe pairing of the drug container and the associated medical delivery device, thus it is possible to ensure that only the correct, intended drug is used as a safety action can be performed should a faulty drug container be inserted. For instance the medical delivery device may incorporate a control circuit which can be adapted to emit an alarm or it can proceed to a safety mode where drug delivery is not possible.

In certain embodiments, the medicament container according to the second aspect, may include a actuator mechanism for controlling the delivery of the medicament from the container and may include control circuitry having activation means operable to emit the field suitable to cause the electrically operable transponder device of the medicament container to emit the at least one measured parameter value, and receiving means for receiving the data thus emitted.

These features are possible to achieve in a safe and low cost fabrication solution when the sensor unit is connected to, or in itself is a RFID (Radio Frequency IDentification) unit thereby consituting a sensor system. A RFID enables the sensor unit to be supplied with energy without the need for wired connection as well as enables the sensor unit to transmit data wirelessly such as a sensed value or a code which can then be received by a control circuit in the medical delivery unit. As the RFID picks up a small amount of energy when it is exposed to a radio frequency signal, the RFID can be adapted to supply energy to a sensor connected to the RFID. Another possibility is to integrate the sensor so it becomes a part of the RFID itself. In both embodiments, the need for a dedicated power supply for the sensor system such as a battery is dispensed with.

The sensor system according to the first and the second aspect may be adapted to sense any kind of physical or chemical parameter value which may be of relevance of the drug contained or particular values related to conditions for the delivery of the fluid. The parameter can for instance relate to pressure, force, temperature, electrical resistance, translucency, electrical conductivity, capacitance, pH, dissolved oxygen, flow or any other parameter value of relevance for the drug and the dispensing thereof. Also, the sensor may be adapted to detect more than a single parameter, e.g. a combination of particular parameter values of said physical or chemical values. Especially values relating to the pressure in the liquid is of interest, as this provides information about a possible leak or occlusion anywhere in the delivery path from the liquid drug container to the user. The normal infusion or injection pressure for a given drug, liquid outlet path (butterfly hose, needle etc.) liquid outlet size and injection or infusion body counter-pressure is known or can be iterative determined as well as calibrated for a given medical drug delivery device configuration. On this basis a pressure window with high and low limits can be determined for the device. In relation to and during a liquid drug delivery the liquid pressure can be monitored in real-time. A pressure within the window indicates acceptable delivery conditions i.e. no leaks and no occlusion. A pressure above the high limit of the window will indicate an occlusion and preventive measures such as alarms and safety stop can be taken. A pressure below the low limit of the window will indicate that there is a leak along the fluid path or in the container itself. The pressure can be monitored in relation to a drug delivery, but it is also a possibility to monitor the pressure at all times or for instance with intervals, which will allow for discovering leaks at all times. An important feature of the pressure monitoring is further, that more than two border limits can be applied. For instance two lower limits of different size can be applied. In this way a pressure below the lowest limit will indicate a leak, whereas a pressure between the lowest limit and a relatively higher low limit will indicate that a drug delivery outside a users body is being performed. This is an important feature in intelligent medical drug delivery devices where a log is kept for automatically keeping track of infused/injected drug and thus it is important to disregard a potential priming (an "airshot") of the medical device which is common before an infusion or injection.

Pressure monitoring can according to the present invention be performed by means of a pressure sensor connected to a RFID, the RFID will then transmit a value relating to the measured pressure to the medical delivery device. It is also possible to integrate the pressure sensor in the RFID. As the RFID can comprise a capacitor, this can be simple, safe and cost efficient implemented as the capacitor itself can be variable and pressure sensitive.

Apart from pressure, a further range of values may also be relevant to measure. Measuring of temperature can be relevant, as many liquid drugs are temperature sensitive. It can be crucial that the drug has been kept under appropriate temperature to ensure that the potentially vital drug delivered is actually active and the delivered dose is corresponding the intended treatment. Appropriate quality of the drug can possibly further be detected via electrical conductivity measurements, translucency, capacitance, pH or dissolved oxygen, thus sensors adapted to measure these values can also be pertinent. Further embodiments of the present invention may comprise a sensor for sensing the drug contained in the container so as to analyze its constituents. Still further embodiments may comprise a sensor for sensing air present in the container, e.g. so as to provide information regarding the need for purging the container before administration. Such sensor may employ a pair of conducting electrodes separated by a small distance and arranged at the container interior for fluid-contact, e.g. placed at the interior surface of a cartridge septum or placed at the interior surface of a slidable plunger. In such a system, during normal operating conditions, the liquid drug will act as a short-circuit, but breaking the circuit whenever air-bubbles surround one of the electrodes. One of said electrodes may be constituted by a needle penetrating the septum. Still further embodiments may comprise a sensor which is able to detect the position or movement of a plunger or plunger rod inside a cartridge. A still further embodiment may comprise a sensor system configured as a switch wich is able to detect whether or not a plunger rod of the actuation mechanism is in contact with the plunger of the cartridge. Such sensor system may be attached or integrated either in the plunger or the plunger rod of the actuator mechanism.

In accordance with the first and second aspect, in relation to the present invention, the term "control circuitry" means any kind of circuitry which is adapted to emit a suitable field such as an electromagnetic field for driving the transponder device, and which is able to receive a response from the transponder device.

In one simple form, the control circuitry is adapted to store the measured values in an internal storage for later recall. Alternatively, or in addition, the control circuitry is adapted to process the measured value, to compare it with pre-defined stored values and to provide an alert to the user of the device, if the measured value falls outside normal operating conditions. Still, alternatively, or in addition, the control circuitry is adapted to further communicate data relating to the measured values to an external device for further data processing.

In accordance with a third aspect, the invention relates to a way to measure pressure in a low cost manner is to take advantage of the features already present in some common drug containers: drug containers comprising a pierceable septum in the outlet end of the container. The pierceable septum is in common configurations flexible and therefore the pressure of the liquid drug has an impact on the septum, as the septum will tend to deform, to curve outwards when the internal liquid pressure is above the surrounding atmospheric pressure. In one embodiment of the present invention, this deformation is exploited to measure the liquid drug pressure by means of a strain-sensitive sensor system arranged at or in the container septum. The strain-sensitive sensor system may involve a conductivity-measurement of conducting particles integrated in the septum, as the conductivity changes when the distance between the particles changes due to deformation of the septum. The strain-sensitive sensor system may be adapted to communicate with a control circuitry of an associated medical delivery device by wireless communication as defined above by the first and second aspect of the invention. Alternatively, the strain-sensitive sensor system may be communicating with the control circuitry by means of a wired connection.

FEATURES OF THE INVENTION

1. A medical delivery device comprising a drug container for fluid drug, the drug container is suited for connection to a fluid outlet, whereby the fluid drug can be transferred out through the outlet, the medical device further comprises an actuator for transferring said fluid drug and a receiver for receiving a signal from a sensor unit, characterised in that said sensor unit is adapted to sense a physical or chemical value and adapted to transmit a wireless signal corresponding said value to said receiver, and the sensor unit is adapted to receive the energy required to sense said value and transmit said corresponding signal wireless by means of electro-magnetic induction.

2. A medical delivery device according to feature 1 characterised in that said sensor is an integrated part of said drug container and that said sensor is an integrated part of a Radio Frequency IDentification (RFID) unit or connected to a RFID unit, whereby transmitting of the value can be performed wireless from the sensor unit to the receiver.

3. A medical delivery device according to feature 1 characterised in that said sensor is an integrated part of a RFID unit or connected to a RFID unit in physical connection to said actuator, whereby the force exercised by the actuator can be sensed and transmitted wireless from the sensor unit to the receiver.

4. A medical delivery device according to any of the preceding features characterised in that said sensor unit further comprises an electronic storage system to store encoded information relevant to the drug container and the sensor unit is adapted to transmit said information wireless.

5. A medical delivery device according to any of the preceding features characterised in that said sensor unit comprises a pressure or force sensor, whereby the pressure in the fluid drug or the force acting on the drug via the actuator can be monitored.

6. A medical delivery device according to any of the features 1-4 characterised in that said sensor is adapted to monitor one or more of the following values: conductivity, impedance, capacitance, temperature, translucency, pH, dissolved oxygen, hydraulic pressure and linear force.

7. A medical delivery device according to any of the preceding features characterised in that said sensor unit is located in any of the following positions: a) in-between a piston rod of said actuator and a movable plunger comprised in the drug container, whereby the force acting on said plunger can be measured, b) integrated with said plunger, c) on the side of said plunger facing the drug, whereby the pressure in said liquid drug can be monitored, d) free flowing in the liquid drug inside the container, e) connected to the inside wall of the container adapted to be connected to an outlet, f) connected to the outside wall of the container adapted to be connected to an outlet or g) in liquid connection to the outlet or outlet line.

8. A medical delivery device according to any of the preceding features characterised in that said liquid drug container is a cartridge closed in one end with a septum which can be penetrated by a needle to establish an outlet, and closed in the other end by a movable plunger.

9. A medical delivery device according to any of the features 1-7 characterised in that said liquid drug container is a flexible reservoir.

10. A medical delivery device comprising a drug container for fluid drug, the drug container has a variable volume and is closed in one end by a flexible closure adapted to be connected to an outlet, whereby the fluid drug can be pressed out through the outlet when the container volume is reduced, the medical device further comprises an actuator for reducing the volume of said container and a receiver for receiving a signal from a sensor unit, characterised in that said sensor unit is an integrated part of said flexible closure, said sensor has a variable resistance or capacitance corresponding the deflection of said flexible closure, whereby the pressure or force acting on the flexible closure by the liquid drug can be monitored.

11. A medical delivery device according to feature 10 characterised in that said sensor comprises two polymer membranes with conducting particles integrated in each of the membranes, the two membranes is parted by an insulating layer to avoid electrical contact from one membrane to another, the sensor is adapted to be penetrated by a conducting needle, whereby electrical contact from one membrane to the other is established when the conducting needle penetrates the membranes.

12. A fluid drug container for a medical delivery device according to any of the preceding features characterised in that the fluid drug container comprises a sensor unit which is an integrated part of the drug container, said sensor unit is adapted to sense a physical or chemical value, and adapted to transmit a wire-less signal corresponding said value to the receiver of said medical delivery device, where the energy required to sense said value and transmit said corresponding signal is supplied wire-less to the sensor unit by means of electro-magnetic induction.

13. A fluid drug container according to feature 12 characterised in that said sensor is an integrated part of a Radio Frequency IDentification (RFID) unit or connected to a RFID unit, whereby transmitting of the value can be performed wireless from the drug container to the receiver.

14. A fluid drug container according to any of the features 12 or 13 characterised in that said sensor unit further comprises an electronic storage system to store encoded information relevant to the drug container and the sensor unit is adapted to transmit said information wireless.

15. A fluid drug container according to any of the features 12-14 characterised in that said sensor unit comprises a pressure or force sensor, whereby the pressure in the fluid drug or the force acting on the drug via the actuator can be monitored.

16. A fluid drug container according to any of the features 12-14 characterised in that said sensor is adapted to monitor any of the following values conductivity, impedance, capacitance, temperature, translucency, pH, dissolved oxygen, pressure and force.

17. A fluid drug container according to any of the features 12-16 characterised in that said sensor unit is located in any of the following positions:
  in-between a piston rod of the actuator of said drug delivery device and a movable plunger comprised in the drug container, whereby the force acting on said plunger can be measured
  integrated with said plunger
  on the side of said plunger facing the drug, whereby the pressure in said liquid drug can be monitored
  free flowing in the liquid drug inside the container
  connected to the inside wall of the container adapted to be connected to an outlet
  connected to the outside wall of the container adapted to be connected to an outlet
  in liquid connection to the outlet or an outlet line 18. A fluid drug container according to any of the features 12-17 characterised in that said liquid drug container is a cartridge closed in one end with a septum which can be penetrated by a needle to establish an outlet, and closed in the other end by a movable plunger.

19. A fluid drug container for a drug delivery device according to any of the features 1-11, the fluid drug container is closed in one end by a flexible closure adapted to be connected to an outlet, whereby the fluid drug can be pressed out through the outlet when the container volume is reduced characterised in that said fluid drug container comprises a sensor unit which is an integrated part of said flexible closure, said sensor has a variable resistance or capacitance corresponding the deflection of said flexible closure, whereby the pressure or force acting on the flexible closure by the liquid drug can be monitored.

20. A fluid drug container according to feature 19 characterised in that said sensor comprises two polymer membranes with conducting particles integrated in each of the membranes, the two membranes is parted by an insulating layer to avoid electrical contact from one membrane to another, the sensor is adapted to be penetrated by a conducting needle, whereby electrical contact from one membrane to the other is established when the conducting needle penetrates the membranes.

DESCRIPTION OF THE DRAWINGS

Embodiments of the invention will now be exemplified with reference to the drawings, in which:

FIG. 4a is a sectional view of a pressure sensor configuration in relation to a liquid drug cartridge according to a second embodiment, while

DESCRIPTION OF EXEMPLARY EMBODIMENTS

Figure 1:
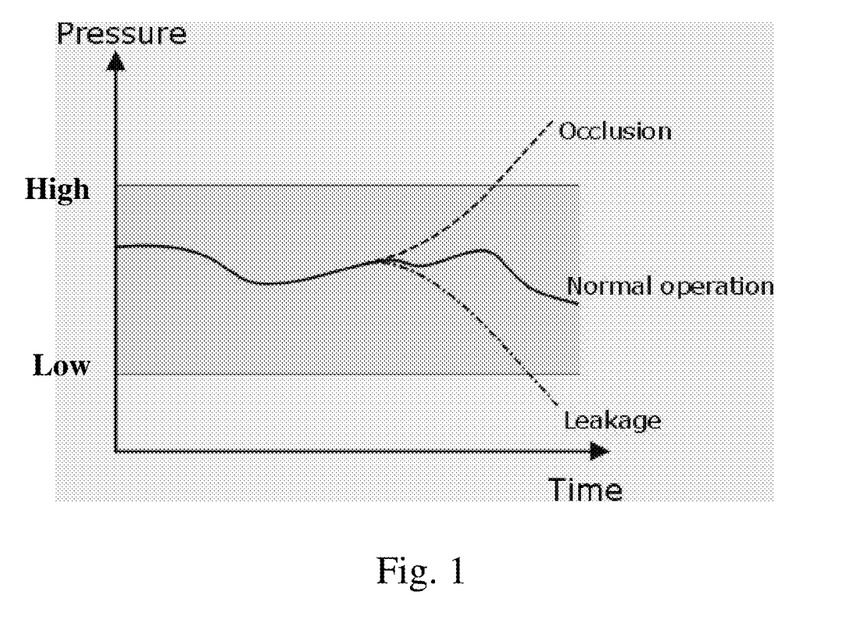
FIG. 1 is a diagram representation of an infusion or injection sequence.

In FIG. 1, a diagram shows an example of an injection procedure performed with a medical delivery device. The hydraulic pressure in the liquid drug cartridge is depicted as a function of injection time. In normal operation of the injection device, the hydraulic pressure in the drug cartridge will fluctuate due to the variation in injection force from the device/user, varying back-pressure from the users tissue and other variations, but the pressure will fluctuate inside the window of the "low" and "high" limits defined for the system on the background of device-individual or general calibration. Should however an occlusion occur somewhere along the liquid path from the drug cartridge via the outlet and through the needle, the hydraulic pressure will rise above the "high" limit and pass outside the allowable window. If on the other hand a leakage occurs, the hydraulic pressure will pass down through the "low" limit and end outside and on the low side of the allowable pressure window. Both scenarios are serious and can lead to a wrong dosage or missing dose of vital medicine, which is why the described monitoring of the pressure is crucial. The monitoring need not only be a real-time monitoring during injection, but can also be an interval monitoring which will then especially reveal a leak in the system. Furthermore, the monitoring may also be carried out during storage of the device, i.e. when the device is not actively being used.

It should be noted that, for some embodiments of medical delivery devices having automated injection procedure such as by means of a motor or a spring-actuated drive mechanism where injection speed can be predicted in a well defined way, the above allowable pressure limits may be defined in advance prior to operating the device. In alternative embodiments, e.g. in manually operated (manually driven) injection devices, the drive mechanism may include further sensor circuitry which provides information about a speed of the injection movement, which then can be used for setting up proper allowable pressure limits.

According to the present invention, to enable monitoring of pressure or other physical or chemical parameter values related to the use of the medical delivery device, a transponder or RFID-based solution may be considered as it provides a simple, reliable, and low-cost solution, has a low power consumption and which is uncomplicated to incorporate in relation to practical embodiments of a medical delivery system, e.g. by incorporation in a drug container.

Reference is made to WO application No. 94/25089 which relates to transponder solutions for transferring static data from a syringe to a syringe pump, the cited document being incorporated herein by reference.

A passive RFID (Radio Frequency Identification) consists of a resonating circuit coupled to a simple IC (Integrated Circuit). The power is supplied by a reader via electromagnetic inductance. The high frequency signal transmitted by the reader is used to charge up a capacitor, resulting in a DC voltage, which in turn is used to power and operate the IC.

Figure 2:
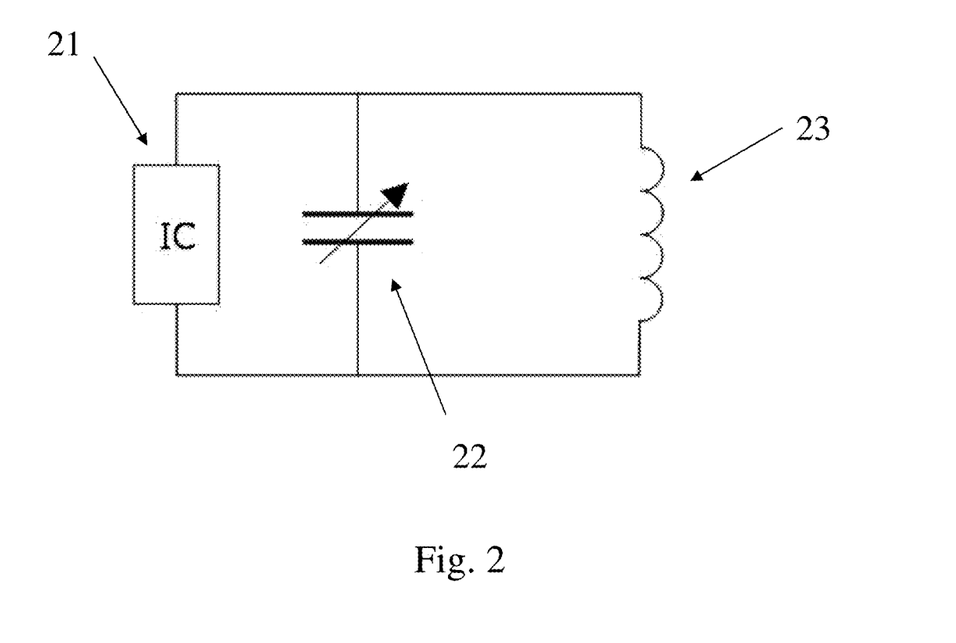
FIG. 2 is a principle drawing of a RFID.

A principle drawing of a RFID incorporating a parameter value sensor is shown on FIG. 2. Position 21 shows an integrated circuit, IC, connected to a coil, position 23 for inductively coupling the RFID to the emitting power source in the medical delivery device and variable capacitor, position 22, acting as a sensor. In this configuration the coil (23) provides power to the RFID, the variable capacitor (22) provides for a pressure sensor input value to the IC (21) which modulates the signal and provides for returning of a value relating to the pressure via the coil/antenna (23) and back to the medical delivery device. Alternatively, the capacitor can have constant capacitance, in which case a separate sensor unit (not shown) could be used to monitor the pressure. The sensor unit would then be connected for exchanging a pressure signal and for supplying power from the RFID to the sensor unit. In the embodiment where the sensor unit is a separate unit, it could still physically be build together with the RFID to form a small integral unit easy to incorporate in relation to the drug cartridge. Further this embodiment allows for sensors for a range of physical or chemical values other than pressure. The RFID then provides power for the sensor unit and receives signals relating to the one or more values relevant for the drug or the injection. The sensors can be any known sensors and examples of relevant parameter values are: temperature, conductivity, capacitance, translucency, pH, dissolved oxygen.

Figure 3:
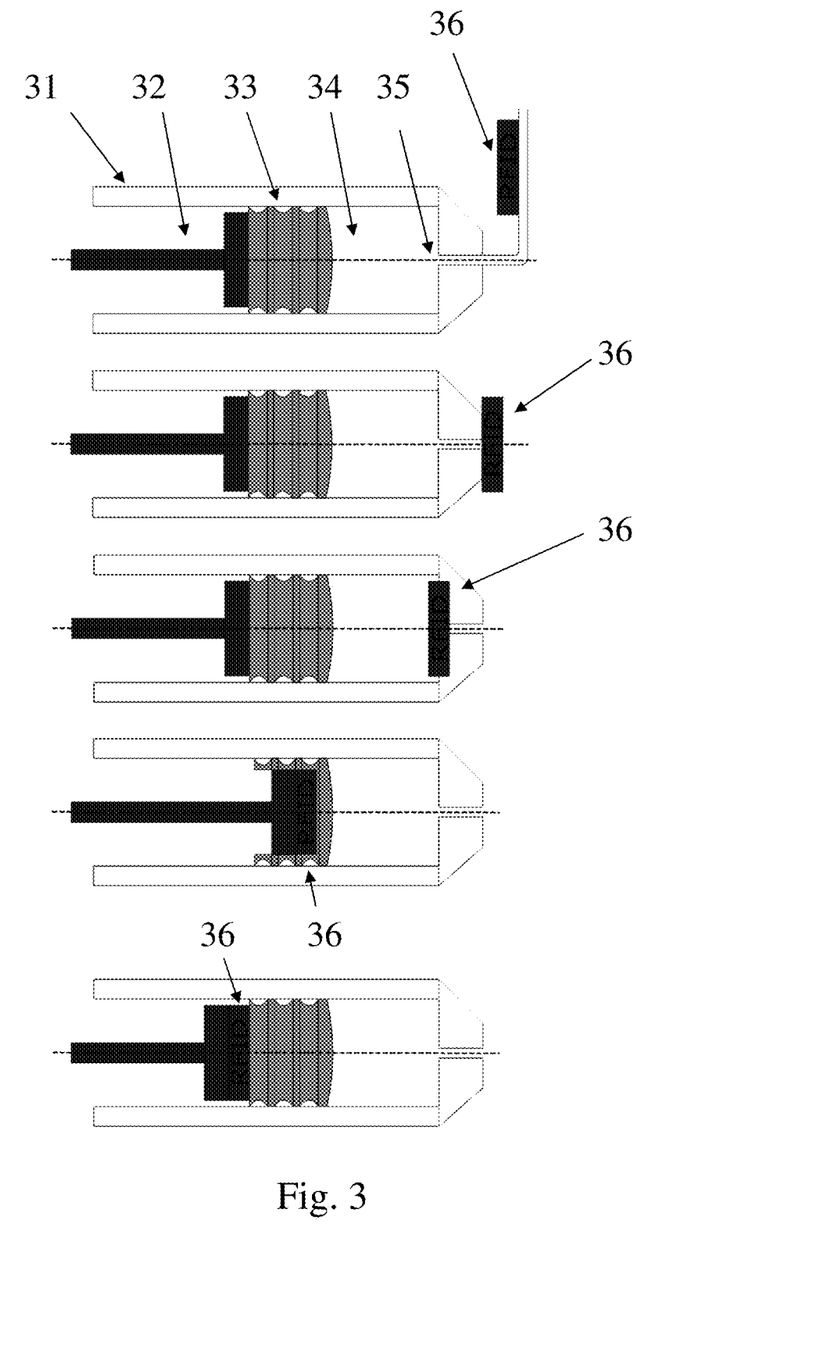
FIG. 3 shows different locations of a RFID in relation to a liquid drug cartridge.

The location of the integral RFID and sensor unit (hereafter named the sensor system, whether the sensor unit is build together with the RFID or it is a part of the RFID as in the case of the variable capacitor) is due to the minute size of the sensor system very flexible. Furthermore, it can be located in the actual environment of the relevant parameter value to be sensed as opposed to a second or third link in a chain relating to the value. As an example, in a cartridge/piston delivery system, when pressure is the relevant value to sense, the sensor system can be placed in the actual liquid where the hydraulic pressure exists and not on the support for a piston rod acting on a piston which in turn acts on the liquid. This eliminates the risk of faulty, deficient or absent signals due to other factors than the actual hydraulic pressure, such as irregular friction, pinching of some of the elements in the force-chain or breakage of some force-chain elements. FIG. 3 shows a range of possible locations of the sensor system (36). In this embodiment the liquid drug reservoir is a drug cartridge 31, closed at the proximal end by a wall except for a liquid outlet (35) and closed in the distal end by a moveable plunger (33) in sealed fit with the inner wall of the cartridge, so a liquid drug (34) can be contained in the cartridge. The plunger can be moved when a force acts on the plunger via an actuator such as a plunger rod (32), the plunger rod can in turn be actuated in any known way i.e. by manual pushing, from a electrical motor, by means of a cocked spring or the like. The sensor system/sensor unit is depicted in FIG. 3 as a disc (36) with rectangular cross section. As can be seen on the five examples of locations, the size of the sensor system enables it to be located in contact with the outlet fluid path, immediately at the outlet in fluid connection, inside the drug cartridge in the liquid chamber in direct contact with the drug, integrated in the moveable plunger between the plunger face and the plunger rod separated from liquid contact but with only minute distance between the pressure sensitive face of the sensor system and the liquid drug separated by a plunger wall and finally the sensor system is shown located between the plunger and the plunger rod. A further location (not shown) is where the sensor system is free flowing inside the drug chamber of the drug cartridge. This is off course possible due to the fact that the sensor system is operative without any wire- or other connection. When the sensor system is free flowing, it is completely exposed to the hydraulic pressure of the drug surrounding the sensor system, and a further advantage is that the sensor system in this way can be utilized as a shaking or agitation ball for drugs that need mixing or agitation prior to an injection.

Whatever location the sensor system has, the integration of the sensor with the drug cartridge allows for utilizing the sensor system also for encoding of the drug/drug cartridge. As the sensor system comprises an IC, the code can be programmed in the IC. The code can be unique or it can be a general code for the type of drug or the type of cartridge. The code can also contain information about production date or any other relevant information about the drug or cartridge. The medical delivery device can via the RFID receive the code-information, which makes it possible to for instance identify whether the drug is the one programmed in the medical device for the user to use, whether the recommended last usage date has expired, whether the cartridge is compatible with the medical delivery device, whether the drug is the one the user should use on the given time of the day, whether the cartridge should be exchanged because the medical device has calculated that the maximum dosage number is imminent or already reached for a given cartridge etc. A range of information and actions are thus possible from the integrated coding of the cartridge or other drug container also incorporated in the sensor system according to this embodiment of the invention.

Figure 4A:
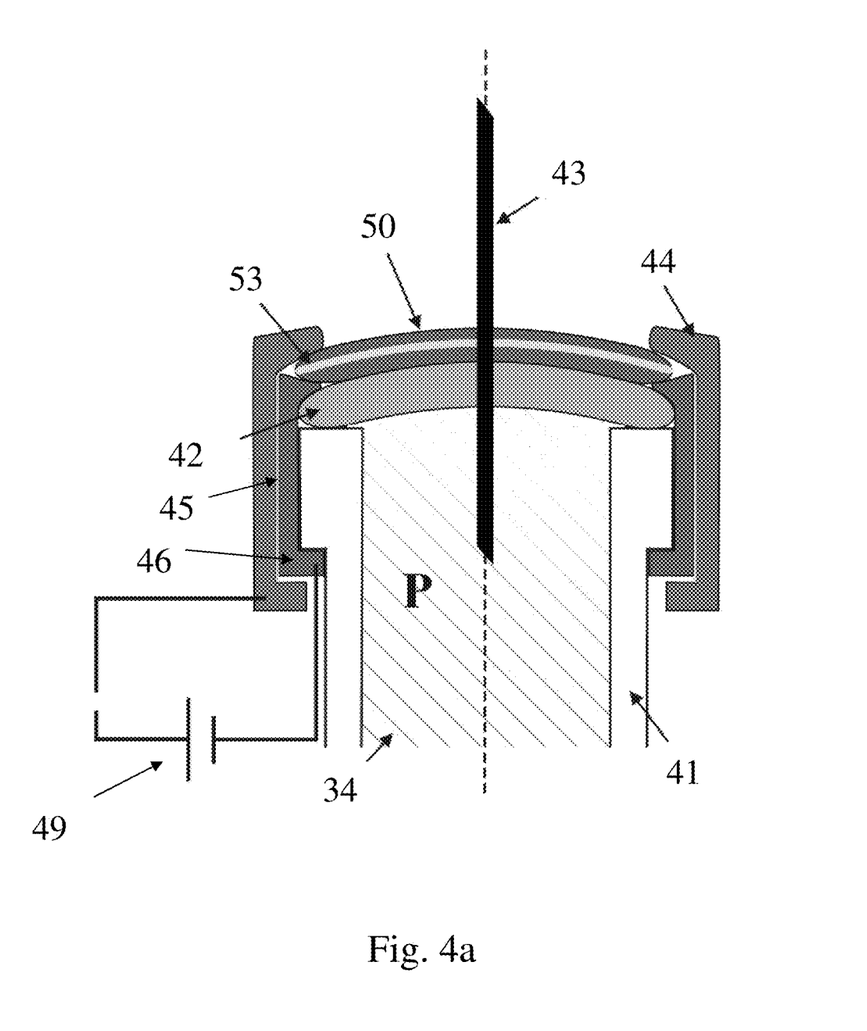

On FIG. 4a a strain-sensitive sensor according to a second embodiment is shown for sensing the hydraulic pressure of a drug in a drug container, here shown as a cartridge, in a reliable and simple way. A cartridge (41) is shown having a drug (34) inside. The cartridge can in the distal end be closed by a moveable plunger (not shown) and in the proximal end (shown) be closed by a penetrable septum (42) in known manner. The rim of the septum (42) is fastened to a distal neck part of the cartridge (41) by means of an electrically conducting swage (46). Additionally, a top is mounted above and outside surrounding the septum, the top comprising a resilient membrane sandwich (50) consisting of two layers (51 and 52) separated by an insulator (53), and mounted on the cartridge proximal end by means of a electrically conductive mantle (44). An electrical insulating layer is arranged between swage (43) and mantle (44).

Figure 4B:
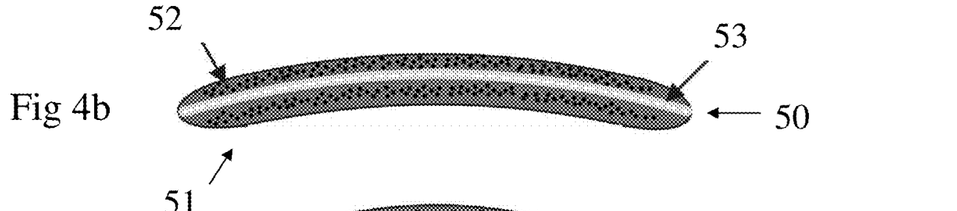
FIGS. 4b and 4c shows enlarged sectional views of the strain-sensitive membrane of the second embodiment, FIG. 5 show a medical delivery device comprising an RFID enabled injection device and a cooperating auxilliary device, and FIG. 6 show a schematic representation of the medical delivery device shown in FIG. 6.
Figure 4C:
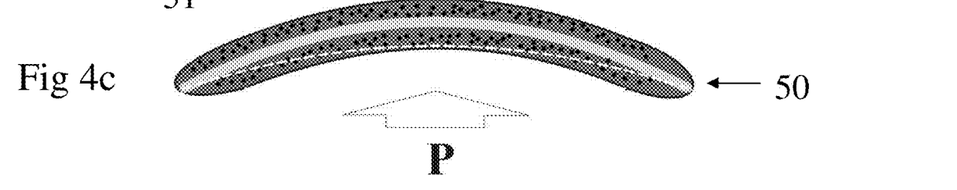

As shown in FIGS. 4b and 4c, which depicts enlarged views of the membrane sandwich 50, each of the two layers (51 and 52) comprise conducting particles in blend with the sandwich material, whereby each of the layers as a whole becomes conductive with a electrical conductivity depending on the density of the particles and therefore depending of the deflection or stretching of the membrane sandwich., Each of the sandwich layers (51 and 52) are electrically connected via respectively the conducting mantle (44) for the outer sandwich layer (51) and the swage (46) for the inner sandwich layer (52). Thus an electrical connection from each sandwich layer can be established to an associated electric circuitry (schematically represented at 49), e.g. to a circuit for supplying a voltage across the membrane sandwich and for measuring the current being drawn by the strain-sensitive membrane sandwich 50. The resistance change may also be measured by e.g. a Wheatstone bridge. Hence, in accordance with the shown embodiment, the pressure sensor is coupled to the electric circuitry by wiring.

In alternative embodiments, a transponder solution as described above, such as by using a passive RFID based sensor system, may be implemented and coupled to the cartridge whereby the sensor system emits measured values to a control circuitry of the medical delivery device upon activation by a suitable electromagnetic field emitted by the control circuitry. As the hydraulic pressure "P" in the liquid drug (34) varies, due to injection resistance, occlusion or leak, the deflection of the septum (42) and the membrane sandwich (50) in contact with the septum varies accordingly. Thus, also the conductivity of the sandwich layers (51 and 52) varies. The two layers are electrically isolated, but as an electrically conductive needle (43) for injection is mounted, penetrating both the membrane sandwich and the septum, electrical connection is established from the rim of the outer sandwich layer to the centre of the outer sandwich layer (51), via the conductive needle to the centre of the inner sandwich layer to the rim of the inner sandwich layer (52), hence the variable conductivity of the membrane sandwich due to the variable deflection of the membrane sandwich according to the hydraulic pressure can be measured. On FIGS. 4b and 4c it is shown how the density of the conductive particles comprised in the membrane layers becomes smaller when exposed to a rising pressure and thus the conductivity of the deflected membrane sandwich shown in FIG. 4c is reduced compared to the conductivity of the less deflected membrane sandwich shown in FIG. 4b.

The strain-sensitive membranes can, e.g., be made out of a flexible insulating polymer material with an admixture of conducting particles, i.e., carbon, gold, silver etc. Alternatively, strips of piezo-resistive material could be incorporated in the polymer membranes, or the membranes could be piezo-resistive themselves. In addition, the cartridge septum itself may include a strain-sensitive material in a single layer with appropriate contact points at two separate locations of the single layer septum. In still alternative embodiments, the septum forms a multi-layer structure with the multiple strain-sensitive layers arranged in parallel with an insulating layer separating the strain-sensitive layers.

To eliminate/reduce built-in or offset stress in the membranes due to the penetrated needle, a relative pressure measurement may be used. A relative measurement between normal operation (membrane penetrated and with an applied pressure from the actuator) and occlusion, and not between an initial situation before the membrane is penetrated (and a pressure applied) and occlusion, eliminates the offset stress.

Figure 5:
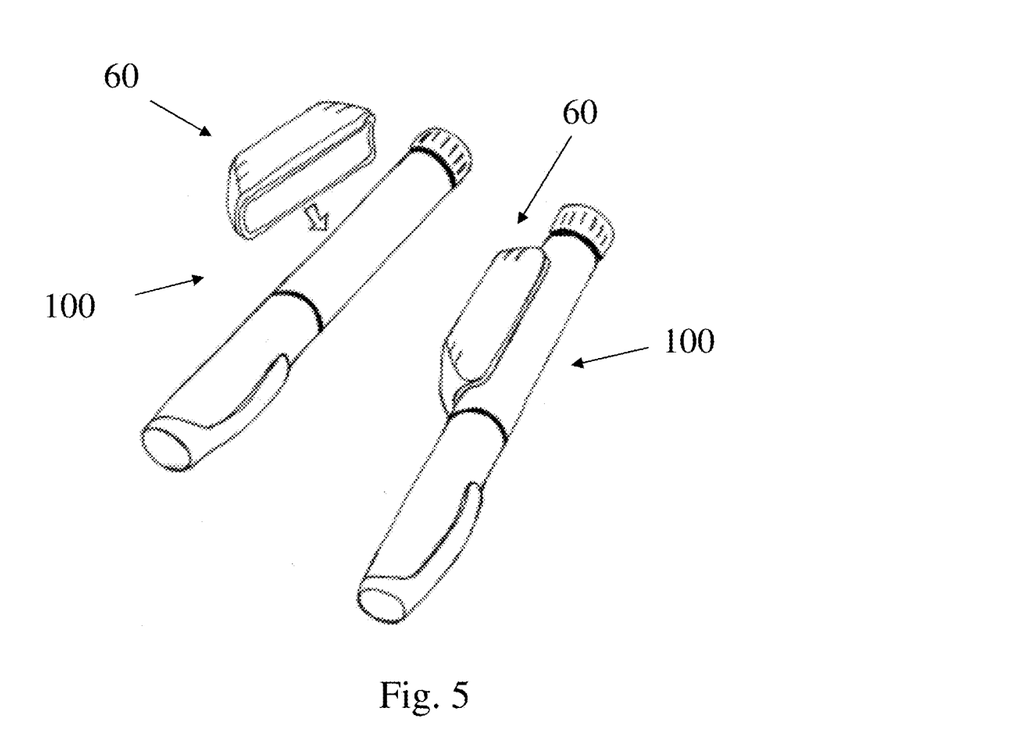
Figure 6:
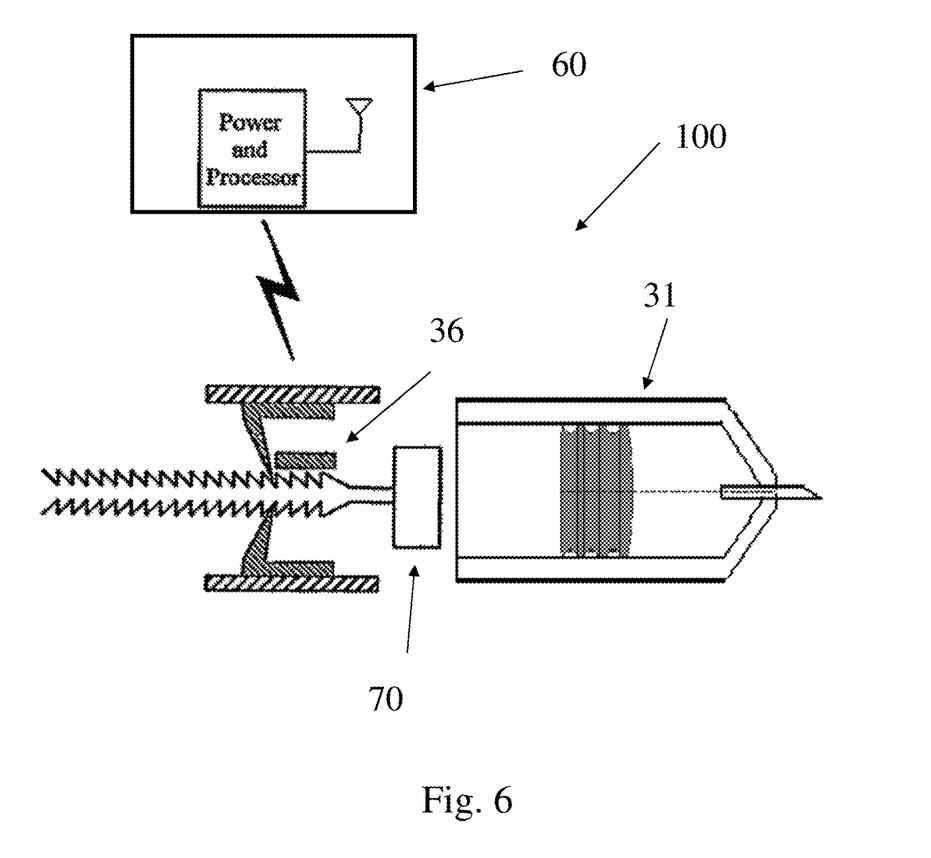

FIG. 5 show a particular embodiment of a medical delivery device consisting of an injection device 100 and an associated auxilliary device 60 adapted to be attached and to cooperate with the injection device. In accordance with the first and second aspect of the present invention, the two sub-assemblies 60 and 100 together constitutes a medical delivery device. FIG. 6 is a schematic representation of the basic components of the medical delivery device. The injection device 100 comprises a drug filled cartridge 31 which includes a slideably arranged plunger in a proximal end and a piercable septum in the distal end for coupling to an injection needle. The injection device 100 comprises a mechanism for setting and injecting a dose of medicament via an actuator mechanism (generally designated 70) in the form of a plunger rod. The actuator mechanism further includes a transponder based sensor system 36 which is used for monitoring movements of the actuator mechanism. In the embodiment shown, the sensor system is based on a passive RFID sensor which has no battery attached to the sensor system. The auxilliary device 60 holds a control circuit which includes a power supply, a radiofrequency transmitter and receiver and antenna means for sending and receiving electromagnetic waves. When the injection device which accommodates sensor system 36 is within operating range of the auxilliary device 60, the emitted field of the transmitter, when activated, is used to power the sensor system 36 of injection device 100 so that the sensor system is able to pick up sensed data regarding various conditions of the injection device. In the depicted embodiment, the sensor system 36 is adapted to monitor movements of the actuator mechanism, and the transponder device of sensor system 36 will emit the data measured for transferring to the receiving means of the auxilliary device 60. In order to use the transmitted data, auxilliary device 60 may include a storage for storing the received data along with other relevant parameters such as the particular time stamps that data is received.

In the depicted form, the auxilliary device 60 attaches mechanically to the exterior of the injection device to ensure that auxilliary device 60 is within working range of injection device 100. Auxilliary device 60 may be provided with user communication means such as a speaker device and/or a display for communicating data related to the data picked up by the receiving means. In addition, auxilliary device 60 may comprise additional communication means for transferring any data related to the use of the device to an external device such as a personal computer or PDA. In alternative embodiments, the auxilliary device 60 is formed as a cap member which is configured for attachment to a distal part of the injection device 100 or is formed as a releasably attachable button member configured to attach to a proximal part of the injection device 100.

The invention claimed is:

1. A medicament container adapted to contain a fluid drug and adapted to cooperate with a medical delivery device for delivering medicament from the container, the medicament container comprising:
   a cartridge which is closed in one end with a pierceable septum and closed in the other end by a movable plunger,
   the medicament container having a sensor system adapted to measure at least one physical or chemical parameter value related with the container and/or the fluid contained therein, wherein the sensor system comprises an electrically operable transponder device to emit the at least one measured parameter value in response to activation by a suitable field applied by an external means, the sensor system being wirelessly powered by the field applied by the external means, and
   wherein the sensor system is part of the septum,
   wherein the septum provides measurement for determining at least one physical or chemical parameter value related with the container and/or fluid contained therein.

2. A medicament container according to claim 1, wherein the piercable septum is flexible and wherein said sensor system comprises a strain-sensitive sensor system arranged at or in the container septum for measuring liquid drug pressure.

3. A medicament container according to claim 1, wherein the sensor system is coupled to or comprised within the medicament container.

4. A medicament container according to claim 1, wherein said sensor system comprises a pressure or force sensor, whereby the pressure in the fluid drug or the force acting on the drug via an actuator of the cooperating medical delivery device can be monitored.

5. A medicament container according to claim 1, wherein said sensor system is adapted to monitor one or more of the parameter values selected from the group consisting of temperature, electrical resistance, electrical conductivity, capacitance, optical translucency, pH, and dissolved oxygen.

6. A medicament container according to claim 1, wherein the sensor system further comprises an electronic storage system to store encoded information relevant to the medicament container and wherein the transponder device is adapted to emit the encoded information in response to activation by a suitable field applied by the external means.

7. A medical delivery device comprising a medicament container according to claim 1, wherein the medical delivery device further comprises control circuitry having activation means operable to emit the field suitable to cause the electrically operable transponder device of the medicament container to emit the at least one measured parameter value, and receiving means for receiving the data thus emitted.

8. A medicament container according to claim 1, wherein the sensor system is arranged in the septum.

9. A medicament container according to claim 1, wherein the sensor system is integrated with the septum.

10. A medical delivery device configured for delivering a fluid drag from a medicament container, the medicament container being:
   a cartridge which is closed in one end with a pierceable septum and closed in the other end by a movable plunger,
   the medical delivery device comprising control circuitry and a sensor system adapted to measure at least one physical or chemical parameter value related with fluid delivery and/or the fluid drag, said sensor system being adapted to transfer said at least one measured parameter value to the control circuitry, wherein
   the sensor system comprises an electrically operable transponder device adapted to emit data including the at least one measured parameter value in response to activation by a suitable field, and wherein
   the control circuitry comprises activation means operable to emit the field suitable to cause the electrically operable transponder device to emit the at least one measured parameter value, and receiving means for receiving the data thus emitted,
   the sensor system is wirelessly powered by the field emitted by the activation means of the control circuitry, and
   wherein the sensor system is part of the septum,
   wherein the septum provides measurement for determining at least one physical or chemical parameter value related with the container and/or fluid contained therein.

11. A medical delivery device according to claim 10, wherein the medical delivery device comprises an actuator for transferring the fluid drug through an outlet and wherein said sensor system comprises a force sensor, whereby the pressure in the fluid drug or the force acting on the drug via the actuator can be monitored.

12. A medical delivery device according to claim 10, wherein said sensor system is adapted to monitor one or more of the parameter values selected from the group consisting of temperature, electrical resistance, electrical conductivity, capacitance, pH, optical translucency, and dissolved oxygen.

13. A medical delivery device according to claim 10, wherein the medical delivery device comprises a first housing part being coupled or being coupleable to the medicament container, the first housing part further holding an actuator mechanism for transferring fluid drug from the container through an outlet, and wherein the control circuitry is contained in a second housing part of the medical delivery device, the second housing part being releasably attachable to the first hosing part.

14. A medical delivery device according to claim 10, wherein the medical delivery device includes a single hand-held housing being coupled or being coupleable to the medicament container, the single hand-held housing holding an actuator mechanism for transferring fluid drug from the container through an outlet and further holding the control circuitry.

15. A medicament delivery device according to claim 10, wherein the sensor system is arranged in the septum.

16. A medicament delivery device according to claim 10, wherein the sensor system is integrated with the septum.

* * * * *